(12) United States Patent
Kuroda

(10) Patent No.: US 8,764,644 B2
(45) Date of Patent: Jul. 1, 2014

(54) ENDOSCOPE LIGHT SOURCE UNIT AND ENDOSCOPY SYSTEM

(75) Inventor: Osamu Kuroda, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 447 days.

(21) Appl. No.: 13/248,703

(22) Filed: Sep. 29, 2011

(65) Prior Publication Data

US 2012/0083656 A1 Apr. 5, 2012

(30) Foreign Application Priority Data

Sep. 30, 2010 (JP) ................................. 2010-222055

(51) Int. Cl.
*A61B 1/06* (2006.01)
*G02B 27/14* (2006.01)
*G02B 21/06* (2006.01)

(52) U.S. Cl.
USPC ........... 600/178; 600/249; 600/117; 362/574; 359/385; 359/634

(58) Field of Classification Search
CPC ...... A61B 5/0084; A61B 1/07; A61B 1/0638; A61B 19/5202; A61B 1/0661; A61B 1/06
USPC ......... 600/178, 476, 160, 478, 101, 339, 117, 600/249; 362/574, 231, 294.01, 611, 327, 362/609; 606/2; 607/2; 348/65; 359/385, 359/584, 201.2, 485.06, 595, 634; 315/149
See application file for complete search history.

(56) References Cited

U.S. PATENT DOCUMENTS

| 5,971,576 | A | * | 10/1999 | Tomioka et al. | 362/574 |
|---|---|---|---|---|---|
| 6,134,365 | A | * | 10/2000 | Colvin | 385/116 |
| 6,826,424 | B1 | * | 11/2004 | Zeng et al. | 600/476 |
| 6,898,458 | B2 | * | 5/2005 | Zeng et al. | 600/476 |
| 7,115,841 | B2 | * | 10/2006 | Zeng et al. | 219/476 |
| 7,215,468 | B2 | * | 5/2007 | Nakata | 359/386 |
| 7,253,894 | B2 | * | 8/2007 | Zeng et al. | 356/326 |
| 7,852,553 | B2 | * | 12/2010 | Tsutsui et al. | 359/385 |
| 2002/0103439 | A1 | * | 8/2002 | Zeng et al. | 600/476 |
| 2004/0019281 | A1 | * | 1/2004 | Weber et al. | 600/476 |
| 2005/0167621 | A1 | * | 8/2005 | Zeng et al. | 250/580 |
| 2005/0203421 | A1 | * | 9/2005 | Zeng et al. | 600/476 |
| 2005/0203423 | A1 | * | 9/2005 | Zeng et al. | 600/476 |
| 2005/0224692 | A1 | * | 10/2005 | Tsuchiya et al. | 250/201.3 |
| 2007/0153542 | A1 | | 7/2007 | Gono et al. | |

(Continued)

FOREIGN PATENT DOCUMENTS

| JP | 2005-342033 A | 12/2005 |
|---|---|---|
| JP | 2005-342034 A | 12/2005 |
| JP | 4009626 B2 | 11/2007 |

*Primary Examiner* — John P Leubecker
*Assistant Examiner* — Ronald D Colque
(74) *Attorney, Agent, or Firm* — Sughrue Mion, PLLC

(57) ABSTRACT

An endoscope light source unit comprising: a first light source section emitting a first illumination light composed of white light; a second light source section emitting a second illumination light orthogonally to a direction in which the first illumination light travels; a light combining member transmitting the first illumination light through a transmission section and, at the same time, reflecting the second illumination light by means of a reflection section to form a combined light so that a beam of the second illumination light may be located in a central part of a beam of the first illumination light; a shaping lens for modifying the beam of the second illumination light emitted; and a condenser lens for converging the combined light.

14 Claims, 5 Drawing Sheets

(56) References Cited

U.S. PATENT DOCUMENTS

| | | | |
|---|---|---|---|
| 2008/0106787 A1* | 5/2008 | Tsutsui et al. | 359/385 |
| 2008/0137362 A1* | 6/2008 | Gjettermann | 362/572 |
| 2008/0180640 A1* | 7/2008 | Ito | 353/31 |
| 2008/0198448 A1* | 8/2008 | Ganser et al. | 359/385 |
| 2010/0268091 A1* | 10/2010 | Takaoka | 600/478 |
| 2010/0321772 A1* | 12/2010 | Reimer et al. | 359/385 |

* cited by examiner

ENDOSCOPE LIGHT SOURCE UNIT AND ENDOSCOPY SYSTEM

BACKGROUND OF THE INVENTION

The present invention relates to endoscope light source units and endoscopy systems allowing an endoscope to be applied in an endoscopic diagnosis to two types of inspection, namely, the inspection with a special light in which a mucosal tissue of the living body is illuminated with light in a specified, narrow wavelength band to obtain information on the tissue at a desired depth, and a normal inspection using visible light for illumination.

An endoscopy instrument used for a conventional endoscopic diagnosis performs a normal inspection, whereupon visible light, such as white light, from a light source unit for an endoscope is guided through a light guide, then emitted through an illumination window at the tip of an insertion section of the endoscope so as to illuminate a target site for inspection, and inspect the target site.

Recently employed for endoscopic diagnosis is an endoscopy instrument capable of performing not only the above normal inspection using white light for illumination but the inspection with a special light in which a biological tissue, such as a mucosal tissue of a body cavity wall, is illuminated with light in a specified wavelength band narrower than the wavelength band of white light (hereafter referred to as "narrow-band light") to obtain information on the biological tissue at a desired depth.

It is readily possible on such an endoscopy instrument as above to visualize biological information unobtainable from conventional inspection images, such as the microstructure of neovascularity occurring in a mucosal layer or submucosa, and the exaggeration of a lesion. If a carcinomatous lesion site is to be inspected, for instance, states of microvessels or microstructures in a superficial layer of a mucosal tissue are observed in more detail by illuminating the tissue with a narrow-band blue light, leading to a more accurate diagnosis of the lesion.

An endoscopy instrument performing inspection not with a narrow-band light but fluorescence as a special light is also employed. In an inspection with fluorescence, a body cavity wall is illuminated with an excitation light to excite a biological tissue, and the variation in intensity of autofluorescence generated by the tissue as excited is utilized to make an earlier finding of a carcinomatous lesion site.

An endoscope light source unit for use in endoscopy instruments performing inspection with fluorescence is disclosed in JP 2005-342033 A and JP 2005-342034 A.

The endoscope light source units as disclosed in JP 2005-342033 A and JP 2005-342034 A each have a white light source emitting white light as visible light, and a semiconductor laser as an excitation light source emitting the excitation light which is light at a shorter wavelength in an ultraviolet region. The optical path from the white light source to the light guide into which the white light is caused to enter is linearly arranged, while the optical path for the excitation light is arranged orthogonally to the optical path for the white light, with the two optical paths being combined together by a dichroic mirror as an optical path-combining element.

In the disclosed units, dichroic mirrors are characterized in that they transmit light at a wavelength equal to or longer than a specified one, and reflect light at a wavelength shorter than the specified one, that is to say, transmit a large proportion of the white light, and reflect the excitation light.

In the inspection with a narrow-band light as described above, a biological tissue is illuminated with only two narrow-band lights, namely, a narrow-band blue light suitable for the inspection of a superficial tissue layer and a narrow-band green light suitable for the inspection of intermediate and superficial tissue layers, without using a narrow-band red light chiefly suitable for the inspection of intermediate and deep layers of a biological tissue, in order to facilitate the inspection of microvessels or microstructures in a superficial layer of the biological tissue. In other words, required for the inspection are only the blue image signals (narrow-band blue light data) obtained by an imaging sensor as a result of the illumination with the narrow-band blue light that chiefly contain information on a superficial tissue layer, and the green image signals (narrow-band green light data) obtained by an imaging sensor as a result of the illumination with the narrow-band green light that chiefly contain information on intermediate and superficial tissue layers. With the green image signals being allocated to the red image data of a color image, and the blue image signals to the green and blue image data, a pseudo-color image composed of 3-ch (three-channel) color image data is produced, and displayed on a monitor, for instance (see JP 4009626 B).

In the technology as disclosed in JP 4009626 B, the two narrow-band lights used for the inspection with a narrow-band light, the narrow-band blue light and the narrow-band green light, are emitted frame-sequentially by using a color filter to switch, in a time-sharing manner, the light from a white light source to be used for the inspection with a normal light. In this connection, in the inspection with a normal light also, light from a white light source is switched by means of a color filter in a time-sharing manner to frame-sequentially emit red, green, and blue lights.

In the endoscope light source units as disclosed in JP 2005-342033 A and JP 2005-342034 A, both adapted for the inspection with autofluorescence as a special light, the excitation light to be used is light at a shorter wavelength in an ultraviolet region and, accordingly, a light component within a specified wavelength range in the visible spectral region of the white light will not be lost when the white light and the excitation light are combined together by the dichroic mirror. On the other hand, in the endoscope light source unit adapted for the inspection with a narrow-band light in a visible spectral region as a special light, to which the technology as disclosed in JP 2005-342033 A and JP 2005-342034 A is applied, white light and the narrow-band light are combined together by a dichroic mirror. Consequently, light in the same wavelength band as the narrow-band light will be lost from the white light which is emitted from the endoscope light source unit when the source of the narrow-band light is switched off.

In other words, if a normal inspection is conducted using an endoscope provided with such an endoscope light source unit as above, the light quantity of white light is considerably reduced in the wavelength band to which a narrow-band light is attributed (specified wavelength range). As a result, an image of the object to be imaged or inspected is obtained as much reduced in accuracy than usual and rendered darker as a whole, which may cause a false diagnosis, such as overlooking of a lesion.

In addition, in the technology as disclosed in JP 4009626 B, the narrow-band lights used for the inspection with a special light are each light in a wavelength band narrower than that of the white light (including RGB lights) emitted during the normal inspection, so that the output light quantity of a narrow-band light source is reduced as compared with that of a white light source, thus rendering an image displayed on a monitor darker as a whole than that displayed during the normal inspection.

If, during the inspection with a special light as described in the reference, the output from the narrow-band light source in itself is raised, that is to say, the output light quantity is increased with respect to narrow-band lights in order that an image displayed on a monitor is made brighter, and light quantity shortages are covered, more heat will be generated at the tip of an endoscope, leading to an unwanted thermal load on the living body as a target for inspection. Such thermal load may not only affect the living body, damage it for instance, but cause the deterioration of the endoscope in itself and, then accordingly, of the endoscopy instrument, with its service life being greatly shortened.

Moreover, it is difficult to apply the technology of JP 2005-342033 A and JP 2005-342034 A to the endoscopy instrument as disclosed in JP 4009626 B because the light quantity of white light is considerably reduced in a specified wavelength range during a normal inspection conducted using an endoscope provided with the light source unit of JP 2005-342033 A or JP 2005-342034 A, as described above.

SUMMARY OF THE INVENTION

An object of the present invention is to provide an endoscope light source unit allowing a normal inspection to be conducted without reduction of white light in light quantity in a specified wavelength range, an inspection with a special light to be conducted without imposing any unwanted thermal load on the living body as a target for inspection, and images of high accuracy to be obtained during both the inspection with a special light and the normal inspection.

Another object of the present invention is to provide an endoscopy system including such an endoscope light source unit as above.

In order to achieve the above objects, the present invention provides an endoscope light source unit, comprising:

a first light source section emitting a first illumination light composed of white light;

a second light source section emitting a second illumination light composed of a narrow-band light in a wavelength band narrower than that of the first illumination light, orthogonally to a direction in which the first illumination light travels;

a light combining member positioned at an intersection of the first and second illumination lights in such a manner that it is tilted at an angle of 30° to 60° to the direction in which the first illumination light travels, which member has a reflection section located in its center for reflecting at least the second illumination light, and a transmission section surrounding the reflection section for transmitting the first illumination light, the light combining member transmitting the first illumination light through the transmission section and, at the same time, reflecting the second illumination light by means of the reflection section to form a combined light of the first and second illumination lights so that a beam of the second illumination light may be located in a central part of a beam of the first illumination light;

a shaping lens for modifying the beam of the second illumination light emitted from the second light source section so that the beam may be substantially equal to the reflection section of the light combining member in shape and size; and a condenser lens for converging the combined light formed by the light combining member so that a beam of the combined light may have a size substantially identical to a size of an entrance face of a light guide in an endoscope, and the beam of the second illumination light in the combined light may be incident on a center of the entrance face of the light guide.

DETAILED DESCRIPTION OF THE INVENTION

In the following, the endoscope light source unit according to the present invention is detailed in reference to the preferred embodiment as depicted in the accompanying drawings.

Figure 1:
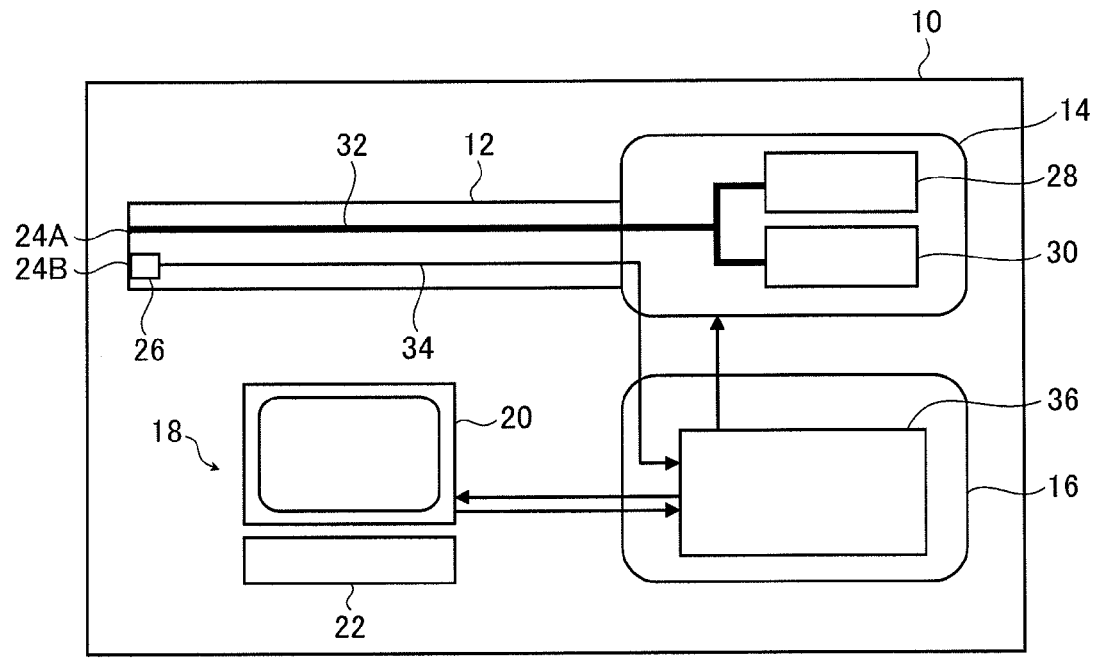
FIG. 1 is a block diagram showing a general configuration of an embodiment of the endoscopy system including the endoscope light source unit of the present invention.

FIG. 1 schematically shows a general configuration of an endoscopy system 10 as a preferred embodiment.

The endoscopy system 10 has an endoscope 12, an endoscope light source unit 14, a processor 16, and an input-output unit 18.

The endoscope light source unit 14 and the processor 16 constitute a control device for the endoscope 12, with the endoscope 12 being optically connected with the light source unit 14, and electrically connected with the processor 16. The processor 16 is also connected electrically with the input-output unit 18 and the light source unit 14. The input-output unit 18 includes a display (monitor) 20 for displaying output image information and so forth, a recording section (not shown) for outputting image information and so forth, and an input terminal 22 serving as a user interface (UI) device accepting input operations, such as mode selection, that is to say, selection from among the normal inspection mode (hereafter also referred to as "normal light mode"), the mode for inspection with a special light (hereafter also referred to as "special light mode"), and so forth, and setting of functions.

The endoscope 12 is the electronic endoscope which has an optical system for illumination including an optical fiber 32 for emitting an illumination light from its tip, and an optical system for imaging including an image pickup device (image sensor) 26 for imaging the region to be inspected, and a scope cable 34. The endoscope 12 also has an insertion section to be inserted into a subject, a manipulation section for manipulating a tip portion of the insertion section into bending, or performing inspective manipulations, and a connector section for detachably connecting the endoscope 12 with the light source unit 14 and the processor 16 of the control device, with none of these sections being shown in the figure. Although not shown either, various channels, including the forceps channel into which a tissue sampling tool and so forth are to be inserted, and a channel for air or water supply, are provided in the interior of the manipulation and insertion sections.

As shown in FIG. 1, an illumination port 24A for illuminating the region to be inspected with light is provided at the tip of the endoscope 12, and the image pickup device 26 for obtaining image information on the region to be inspected, which may be a monochromatic charge-coupled device (CCD) image sensor or a complementary metal oxide semiconductor (CMOS) image sensor, is positioned in a light receiving section 24B adjacent to the illumination port 24A. The illumination port 24A of the endoscope 12 is provided with a cover glass and a lens (neither being shown) constituting an optical system for illumination, while an objective lens unit (not shown) constituting an optical system for imaging is placed in the light receiving face of the image pickup device 26 in the light receiving section 24B.

The insertion section of the endoscope 12 is so manipulated with the manipulation section as to be flexible, that is to say, bendable in any direction, and at any angle, appropriate to the site in the subject to which the endoscope 12 is to be applied, or the like. In consequence, the illumination port 24A and the light receiving section 24B, namely, the image pickup device 26 positioned therein, can be directed to a desired site to be inspected.

In the endoscope 12, light emitted from the light source unit 14 is propagated through the optical fiber 32 to the tip of the endoscope 12, then emitted through the illumination port 24A toward a desired site to be inspected.

The optical fiber 32 is a bundle of 1000 to 2000 multimode fibers each having a numerical aperture (NA) of 0.3 to 0.6 and a diameter of 30 μm, for instance.

The light coming back from the site to be inspected (object to be imaged) as illuminated with the illumination light forms an image on the light receiving face of the image pickup device 26 through the light receiving section 24B, with the site to be inspected being thus imaged by the image pickup device 26.

After imaging, an image signal representing the obtained image is outputted from the image pickup device 26, and inputted into an image processing system 36 of the processor 16 through the scope cable 34.

Figure 2:
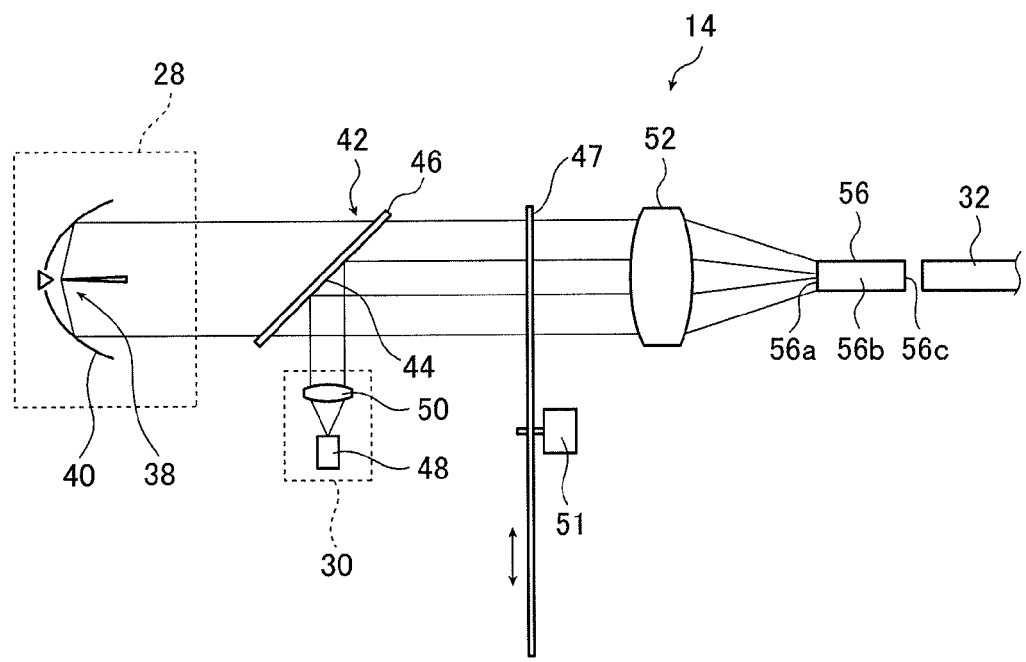
FIG. 2 is a schematic view illustrating the details of the endoscope light source unit as shown in FIG. 1.

The light source unit 14 is described in reference to FIGS. 1 and 2.

FIG. 2 is a schematic diagram showing the configuration of the light source unit 14.

As shown in FIG. 2, the light source unit 14 consists of a first light source section 28, a second light source section 30, a light combining member 42, a rotating filter 47, a condenser lens 52, and a rod integrator 56.

The first and second light source sections 28 and 30 are separately controlled by a light source controlling section (not shown) of the processor 16 with respect to light emission, so that the light quantity ratio between light emitted from the first light source section 28 and light emitted from the second light source section 30 is variable at will.

The lights emitted from the light source sections 28 and 30 are combined together in the light source unit 14, and inputted into the optical fiber 32.

The first light source section 28 includes a xenon light source 38 emitting white light to be used for both the normal light mode and the special light mode, and a reflector 40 as a converging optical element for collecting most of the white light emitted from the xenon light source 38 into a parallel light beam.

Preferred examples of the xenon light source 38 include a 300 W xenon lamp manufactured by PerkinElmer Japan Co., Ltd. Instead of the xenon light source 38, another high-intensity discharge lamp, such as a mercury lamp or a metal halide lamp, may be used as a light source for the illumination with white light.

The reflector 40 is provided in order to emit the white light radiating from the xenon light source 38 as a parallel light beam, and is the parabolic mirror in the embodiment as shown that is positioned so that the arc (white light) generated between electrodes of the xenon light source 38 may be located in the vicinity of the focus of the mirror. The reflector 40 is not particularly limited, with any known reflector capable of collecting the white light radiating from the xenon light source 38 into a parallel light beam being usable.

The second light source section 30 is dedicated to the special light mode, and includes a special light source 48 emitting a narrow-band light, and a collimator lens 50 for collimating the beam of a narrow-band light emitted from the special light source 48 to produce a parallel light beam. The special light source 48 may be a laser light source or LED light source for emitting a narrow-band light, with examples thereof including a semiconductor laser light source emitting a laser beam with a color in a blue to violet spectral region, such as a blue laser light source (445 LD) emitting a blue laser beam and a violet laser light source (405 LD) emitting a violet laser beam, and a blue LED emitting a blue LED light. The collimator lens 50 shapes the beam of a narrow-band light into a beam in a specified, circular or approximately circular shape so that the narrow-band light may be incident on a reflective member 44 in an approximately elliptical shape located in the center of the light combining member 42 which is placed as tilted at an angle of 45° to the optical axis of the narrow-band light.

The special light source 48 is not particularly limited as long as it is a light source emitting a narrow-band light in a wavelength band narrower than that of white light, while a semiconductor source of light in a blue to violet spectral region, such as a blue/violet laser light source (445/405 LD) or a blue LED, is preferred if a superficial tissue layer is to be inspected.

An InGaN laser diode as a broad area laser diode, or an InGaNAs or GaNAs laser diode may be used as a blue/violet laser light source.

The second light source section 30 is positioned at a lateral side of the optical path of the white light emitted from the xenon light source 38 of the first light source section 28 so that the optical path of the narrow-band light emitted from the special light source 48 and shaped by the collimator lens 50 into a beam in a specified, approximately circular shape may be orthogonal to the optical path of the white light, that is to say, the narrow-band light may be incident on the light combining member 42 in a direction orthogonal to the direction in which the white light travels.

The collimator lens 50 shapes the beam of the narrow-band light as emitted from the special light source 48 into a beam in a specified, circular or approximately circular shape so that the beam of the narrow-band light incident on the light combining member 42 as placed in such a manner that it is tilted at an angle of 45° to the direction in which the beam proceeds may be nearly equal to the reflection face of the reflective member 44 in the light combining member 42 in shape and size. A combination of the first cylindrical lens having a power (magnification) only in the minor axis direction that is used to shape the beam of the narrow-band light so that the size as measured in the major axis direction (length of the major axis) of an approximately elliptical shape formed by the incident beam of the narrow-band light may match that of an approximately elliptical shape of the reflection face of the reflective member 44, and the second cylindrical lens having a power (magnification) only in the major axis direction that is used to shape the beam of the narrow-band light so that the size as measured in the minor axis direction (length of the minor axis) of an approximately elliptical shape formed by the incident beam of the narrow-band light may match that of an approximately elliptical shape of the reflection face of the reflective member 44, or a lens suite performing both functions of the above first and second cylindrical lenses may be employed as the collimator lens 50.

It should be noted that the collimator lens 50 is not limited to those shaping the beam of the narrow-band light emitted from the special light source 48 so that the beam incident on the light combining member 42 as placed in a tilted manner may be nearly equal to the reflection face of the reflective member 44 in shape and size, as described above. Any collimator lens is usable which is capable of not only collimating the beam of the narrow-band light to produce a parallel light beam but shaping the beam of the narrow-band light into a beam in a specified, approximately circular shape so that the beam of the narrow-band light may wholly reflect from the reflection face of the reflective member 44 in the light combining member 42.

Moreover, the collimator lens to be used in the present invention is not limited to the collimator lens 50 as used in the shown embodiment which shapes the beam of the narrow-band light as emitted from the special light source 48 into a beam in a specified, approximately circular shape. If the special light source 48 is adapted to emit the narrow-band light whose beam has an approximately circular shape geometrically similar to an approximately circular shape corresponding to the shape of the reflection face of the reflective member 44 in the light combining member 42, a collimator lens used may modify an approximately circular beam of the narrow-band light emitted from the special light source 48 so that the size of the beam may correspond to that of the reflection face of the reflective member 44 in the light combining member 42, while maintaining the shape of the beam, as well as collimate the beam to produce a parallel light beam.

The light combining member 42, which constitutes a feature of the present invention, is positioned at the intersection of the white light emitted from the xenon light source 38 and the narrow-band light emitted from the special light source 48 in such a manner that it is tilted at an angle of 45° to both the directions in which the white light and the narrow-band light travel, respectively. The light combining member 42 transmits the white light in the normal light mode while, in the special light mode, it transmits the white light and, at the same time, reflects the narrow-band light to combine them together. In the embodiment as shown, the light combining member 42 is positioned in the optical path of the white light downstream from the first light source section 28 in such a manner that it is tilted at an angle of about 45° not only to the optical path of the white light but that of the narrow-band light emitted from the second light source section 30. In the present specification, the upstream side of the optical path of the white light refers to the side on which the first light source section 28 is located, with the downstream side referring to the side on which the optical fiber 32 of the endoscope 12 is located. The light combining member 42 will be detailed later.

The rotating filter 47 is positioned downstream from the light combining member 42.

Figure 3:
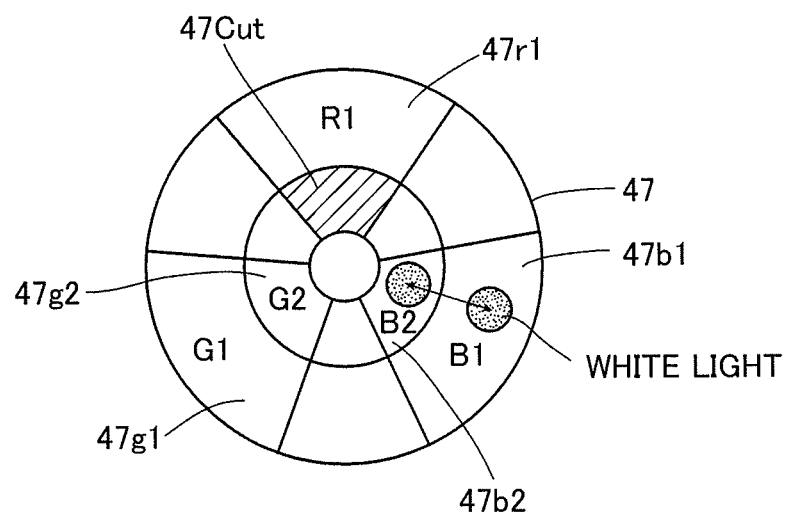
FIG. 3 is a front view showing the structure of a rotating filter used in the endoscope light source unit of FIG. 2.
Figure 4A:
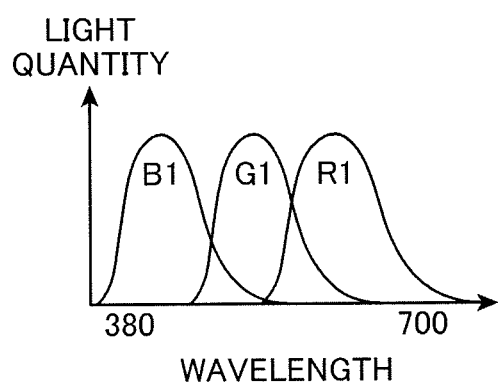
FIGS. 4A and 4B are graphs showing the spectral characteristics of first and second filter sets of the rotating filter as shown in FIG. 3, respectively.
Figure 4B:
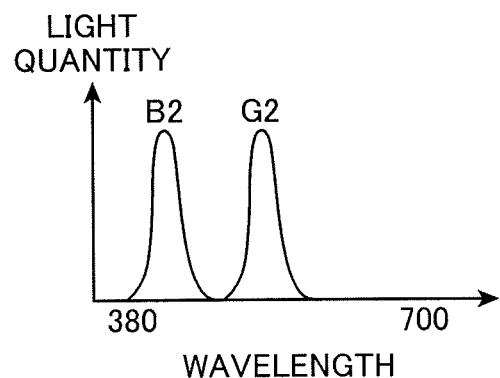

FIG. 3 is a front view showing the structure of the rotating filter 47, and FIGS. 4A and 4B are graphs showing the spectral characteristics of first and second filter sets of the rotating filter 47, respectively.

In the normal light mode, the rotating filter 47 divides the white light as emitted from the xenon light source 38 and transmitted through the light combining member 42 into three color components, namely, red, green, and blue components. In the special light mode, the filter 47 divides a combined light prepared by the light combining member 42 from the white light as emitted from the xenon light source 38 and the narrow-band light as emitted from the special light source 48 into two color components, namely, a narrow-band green component within a wavelength range included in the wavelength range of the green component and, accordingly, being narrower than the latter, and a narrow-band blue component within a wavelength range included in the wavelength range of the blue component and being narrower than the latter.

As shown in FIG. 3, the rotating filter 47 is in the form of a disk with its center serving as a rotation center, and has a dual structure. In the outer part of the dual structure as seen in the radial direction, an R1 filter 47r1, a G1 filter 47g1, and a B1 filter 47b1 are arranged as a first filter set for outputting frame-sequential lights with such overlapping spectral characteristics as shown in FIG. 4A suitable for color reproduction. As seen from FIG. 4A, the R1 filter 47r1 of the rotating filter 47 separates the red component, while the G1 filter 47g1 separates the green component, and the B1 filter 47b1 separates the blue component. In the inner part of the dual structure of the rotating filter 47, a G2 filter 47g2, a B2 filter 47b2, and a light shielding filter 47Cut are arranged as a second filter set for outputting two frame-sequential narrow-band lights with such discrete spectral characteristics as shown in FIG. 4B making it possible to extract information on a desired tissue layer. As seen from FIG. 4B, the G2 filter 47g2 separates the narrow-band green component, and the B2 filter 47b2 separates the narrow-band blue component.

The rotating filter 47 is rotated by a motor 51 controllably driven by a control circuit not shown. In addition, the rotating filter 47 is moved in the radial direction during the switching between the normal light mode and the special light mode as described later by a mode switching motor (not shown) receiving a control signal from the input terminal 22 or the processor 16.

The condenser lens 52 is positioned downstream from the rotating filter 47, and converges the individual color components (hereafter also referred to as "frame-sequential lights") of the white light as transmitted through the light combining member 42 or of the combined light as prepared by the light combining member 42 from the white light and the narrow-band light, that have been separated by the rotating filter 47 from the white light or the combined light, at one end of a rod integrator 56 substantially equal to the optical fiber 32 in size in order to make the components incident on the entrance end face of the optical fiber 32 serving as a light guide.

In other words, the condenser lens 52 converges the individual color components of the white light or the combined light so that the beam of each component may be incident on the entirety of the entrance end face of the rod integrator 56, that is to say, the beam of each frame-sequential light may be nearly equal to the entrance end face of the rod integrator 56 and, accordingly, the entrance end face of the optical fiber 32 in size. In this regard, color components (frame-sequential lights) of the narrow-band light in the combined light are also converged by the condenser lens 52, accordingly, whereupon the beam of each component has such a size that its ratio to the size of the entrance end face of the optical fiber 32 or the rod integrator 56, is the same as the ratio of the size of the beam of the narrow-band light as shaped by the collimator lens 50 to the size of the beam of the white light. The condenser lens 52 thus converges the color components (frame-sequential lights) of the narrow-band light in the combined light so that they may be incident on each center of the entrance end faces of the rod integrator 56 and the optical fiber 32. The condenser lens 52 may be any known condenser lens used in a condensing optical system.

The rod integrator 56 is positioned downstream from the condenser lens 52 so as to cause the individual frame-sequential lights (color components) of the white light or the combined light as transmitted or prepared by the light combining member 42, which have been separated by the rotating filter 47 and converged by the condenser lens 52, to be incident on the entrance end face of the optical fiber 32 in the endoscope 12 while having an equalized in-plane light quantity distribution. To be more specific: The rod integrator 56 has an entrance end face 56a on which the frame-sequential light as converged by the condenser lens 52 should be incident, a main body 56b for multiply reflecting therein the frame-sequential light entering through the entrance end face 56a into the body 56b to equalize the in-plane light quantity distribution, and an exit end face 56c through which the combined light with an equalized light quantity distribution is emitted. The frame-sequential light having entered through the entrance end face 56a into the main body 56b is multiply reflected in the body 56b, so that the light quantity distribution is equalized in the exit end face 56c. The frame-sequential light with the light quantity distribution thus equalized is emitted through the exit end face 56c, and the beam of each frame-sequential light as emitted is wholly incident on the entrance end face of the optical fiber 32 in the endoscope 12.

The rod integrator 56 is nearly equal to the optical fiber 32 of the endoscope 12 in size (diameter), that is to say, the exit end face 56c of the rod integrator 56 has a size nearly equal to that of the entrance end face of the optical fiber 32.

In the rod integrator 56, which is adapted to impart to light emitted through the exit end face 56c an equalized light quantity distribution in the end face 56c by allowing, in the main body 56b, a multiple reflection (repeated total reflection) of light incident on the entrance end face 56a, the angle of incidence of the light incident on the entrance end face 56a is retained for each ray, so that each ray of the incident light is emitted through the exit end face 56c at the same angle as the angle of incidence of the relevant ray.

In the present invention, especially in the special light mode in which the individual frame-sequential lights (color components) of the combined light as prepared by the light combining member 42, that have been separated by the rotating filter 47 and converged by the condenser lens 52, enter into the rod integrator 56, frame-sequential lights of the narrow-band light in the combined light, which are smaller than the frame-sequential lights of the white light in beam thickness on the reflective member 44 in the light combining member 42 as described later, each enter into the rod integrator 56 at a smaller NA than the frame-sequential lights of the white light, and are each emitted through the exit end face 56c at the same NA, with their respective light quantity distributions being equalized in the end face 56c. A restricted light distribution is thus achieved with respect to the narrow-band light, so that heat generated at the tip of the endoscope 12, or the light quantity of the narrow-band light is reduced.

The rod integrator 56 is not particularly limited but may be any known rod integrator commonly used in an optical system for illumination in an endoscopy instrument.

Making reference to FIG. 5, the light combining member 42 is described in detail.

Figure 5A:
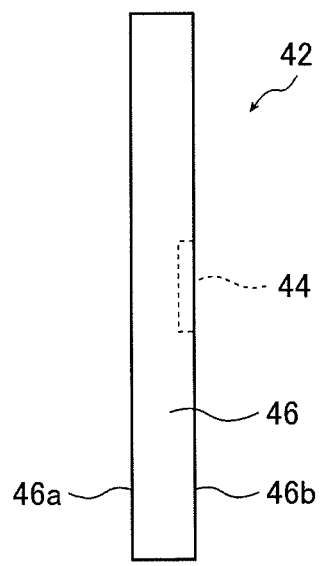
FIG. 5A is a side view of a light combining member used in the endoscope light source unit of FIG. 2.
Figure 5B:
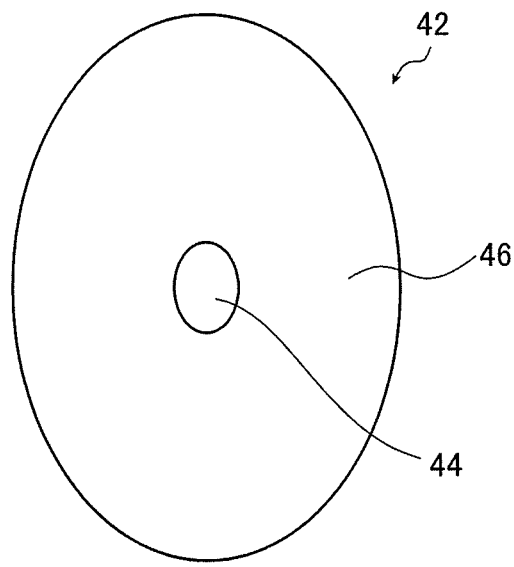
FIG. 5B is a front view thereof.

FIG. 5A is a side view of the light combining member 42, and FIG. 5B is a front view thereof. In FIG. 5A, the side of the member 42 on the left in the drawing is opposite to the first light source section 28 while the side on the right is opposite to the rotating filter 47.

The light combining member 42 is positioned at the intersection of the white light and the narrow-band light in such a manner that it is tilted at an angle of 45° to both the directions in which the white light and the narrow-band light travel, respectively, as shown in FIG. 2 and, as seen from FIG. 5, consists of a transparent member 46 in disk form, and a reflective member 44 provided in the center of one face of the transparent member 46. The light combining member 42 transmits the white light through the transparent member 46 and, at the same time, reflects by means of the reflective member 44 the narrow-band light as shaped by the collimator lens 50 into a beam in a specified, approximately circular shape so that the narrow-band light may travel in a direction almost identical to the direction in which the white light travels, and the beam of the narrow-band light may be located in a central part of the beam of the white light, so as to combine the white light and the narrow-band light together.

The transparent member 46 is a member for transmitting the white light emitted from the first light source section 28, and is not particularly limited as long as it allows transmission of the white light.

While the transparent member 46 as used in the shown embodiment has an approximately elliptical shape, with its minor axis being equal to the thickness of a parallel beam of the white light emitted from the xenon light source 38, and its major axis being $\sqrt{2}$ times as long as the minor axis, the transparent member to be used is not particularly limited in dimension or shape as long as it allows transmission of the beam of the white light, whereupon a transparent member in a square or rectangular shape may also be employed.

If a parallel beam of the white light emitted from the xenon light source 38 has a diameter (2 r) of about 25.4 mm, for instance, a transparent member in an approximately elliptical shape with a minor axis of 25.4 mm (2 r) and a major axis of 35.9 mm (2 r×$\sqrt{2}$), or a transparent member in any shape having larger dimensions, such as in a circular shape with a diameter of not less than 35.9 mm may be used.

In the present invention, it is preferable to provide an antireflective coating on an entrance face 46a and/or an exit face 46b of the transparent member 46. The antireflective coating to be provided is not particularly limited, with any known antireflective coating being usable. An antireflective coating provided makes it possible to prevent the white light from unwantedly reflecting from the entrance face 46a and/or the exit face 46b of the transparent member 46 so as to improve the white light transmission efficiency. The surface reflection is reduced by an antireflective coating by, for instance, about 5% per face.

The reflective member 44 is a light reflecting member in an approximately elliptical shape provided in the exit face 46b of the transparent member 46 so that it may cover a central part of the exit face 46b. The narrow-band light as emitted from the special light source 48 of the second light source section 30 and shaped by the collimator lens 50 into an approximately circular beam is reflected by the reflective member 44 toward the downstream side of the optical path of the white light.

Preferably, the reflective member 44 has shape and size almost identical to the shape and size of a region (reflection region) defined by the beam of the narrow-band light which has been so shaped by the collimator lens 50 as to have an approximately circular shape and is incident on the light combining member 42 placed as tilted at an angle of 45°. It is most preferred in the present invention that the reflective member 44 is identical in shape and size to the reflection region defined by the beam of the narrow-band light incident on the light combining member 42, so that the member 44 may reflect the whole beam of the narrow-band light, although exact identity is not necessarily required. In other words, the shape and size of the reflective member 44 are preferably such that the member 44 is capable of reflecting the whole beam of the narrow-band light.

The reflective member 44 is not particularly limited, and any reflective member is usable as long as it reflects the beam in a specified, approximately circular shape of the narrow-band light as emitted from the second light source section 30 so as to combine the beam of the narrow-band light with a parallel beam of the white light as emitted chiefly from the first light source section 28 so that the former may be located in a central part, especially a portion with a reduced light quantity, of the latter. The reflective member 44 may be a member adapted to reflect the narrow-band light downstream while reflecting or absorbing the white light incident on the light combining member 42 from upstream to prevent a downstream transmission thereof, or alternatively, a dichroic mirror allowing transmission of a component in a part of the wavelength region of the white light, that is to say, a component in the wavelength region of the white light excluding the wavelength region to which the narrow-band light is attributed. If a dichroic mirror is used as the reflective member 44, white light components in the wavelength region excluding the wavelength region to which the narrow-band light to be reflected is attributed can more or less be transmitted also through the reflective member 44, which enables an effective use of the white light and an increase in light quantity of the combined light.

As described before, if the technology as disclosed in JP 2005-342033 A and JP 2005-342034 A is applied to the inspection with a narrow-band light in a visible region as a special light, the light quantity of white light derived from a xenon light source and emitted from an endoscope light source unit is considerably reduced in a specified wavelength range in the normal light mode in which the source of the narrow-band light is switched off. In order to minimize such reduction in light quantity, the present inventor made diligent researches so as to work out the reflective member 44 having the shape as described below.

Figure 6:
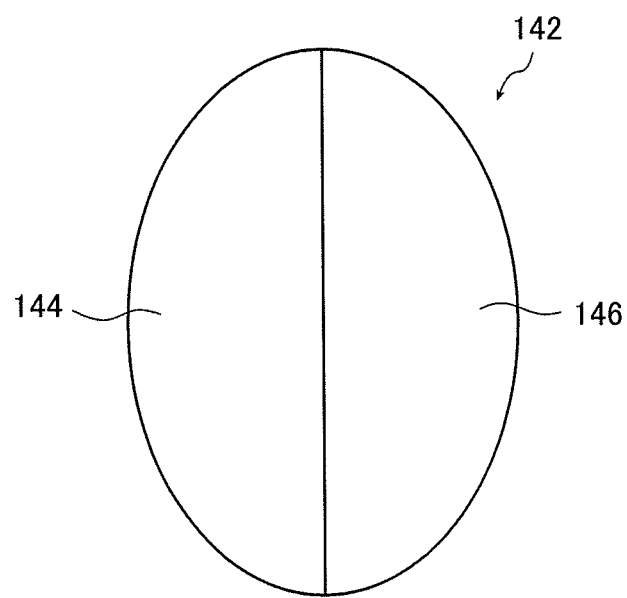
FIG. 6 is a front view of a light combining member used for reference.

The present inventor conducted, for instance, an experiment on the combination of white light and a narrow-band light using a light combining member 142 shown in FIG. 6, which consists of a reflective member 144 in a semielliptical shape occupying half of the area of the exit face, and a transparent member 146 with an area similar to that of the member 144.

In the experiment, the reduction in light quantity of white light in a specified wavelength range in the normal light mode was suppressed as compared with the case where a dichroic mirror so large as to cover the entire cross-section of the optical path of white light is used, such as described in JP 2005-342033 A and JP 2005-342034 A.

Use of such a light combining member as above, however, cannot get rid of the problem as mentioned before, that is to say, will cause, in both the normal light mode and the special light mode, a loss by half of the light quantity of the component of white light from a xenon light source that is attributed to a specified wavelength range, so that an image obtained during an endoscopic inspection is made darker, with a sophisticated diagnosis being thus inhibited.

The present inventor made diligent researches in order to combine white light and a narrow-band light together while minimizing, in both the normal light mode and the special light mode, the reduction of white light in light quantity in a specified wavelength range. In a discharge tube commonly used as a white light source, such as a xenon light source, electrodes, namely an anode and a cathode, are present in a central part of a reflector, with the anode passing through a hole with a diameter of about 4.0 mm formed in the central part, so that a parallel beam of the white light emitted from the discharge tube such as a xenon light source lacks parallel rays in its central part with a diameter almost identical to that of the hole as above. It proved advantageous that the reflective member 44 in the light combining member 42 as tilted at an angle of 45° has an approximately elliptical shape and a size corresponding to an approximately circular shape and the size of the central part of the white light where parallel rays are absent, respectively, and the reflective member 44 as such is mounted in the center of the exit face (transmission face+reflection face) of the light combining member 42.

In the present invention, it is preferable that the reflection face of the reflective member 44 in the light combining member 42 that is approximately elliptical in shape has the major axis which is 10 to 50% on the major axis of an approximately elliptical shape formed by the white light transmitted through the transparent member 46 on the transmission face of the member 46.

It is also preferable that the size of the reflection face of the reflective member 44 in an approximately elliptical shape comprises 1 to 25% of the size of the total exit face (the transmission face of the transparent member 46 for emitting white light plus the reflection face of the reflective member 44 for emitting a narrow-band light) of the light combining member 42 for emitting a combined light.

If the 300 W xenon lamp manufactured by PerkinElmer Japan Co., Ltd. as mentioned before is used in the first light source section 28 in the shown embodiment, for instance, a parallel beam radiating through a radiation window of the lamp has a diameter defined by the dimensions of the window, diameter of 25.4 mm. On the other hand, since electrodes, namely an anode and a cathode, are present in the center of the 300 W xenon lamp, and the reflector 40 has a hole with a diameter of about 4.0 mm formed in its central part so that the anode may pass through the hole, white light cannot be emitted from the central part of the reflector 40. In other words, the beam of the white light as emitted from the xenon lamp has in its central part the region where rays of the white light are absent, a part without xenon lamp light having a diameter of about 4.0 mm, for instance.

If the narrow-band light from the second light source section 30 is combined with the white light so that it may be located in the part with a diameter of about 4.0 mm in the center of the beam of the white light where rays of the white light are absent, a combined light is attained from the white light and the narrow-band light without reducing the white light, or even without causing a mutual loss between the two lights.

In that case, the reflective member 44 may be formed in an elliptical shape with a major axis of about 5.7 mm and a minor axis of about 4.0 mm to make it corresponding to the part where rays of the white light are absent.

Thus in the present invention, the beam of the narrow-band light is arranged in the central part of the beam of the white light upon combining the white light and the narrow-band light together into a combined light, so that, during the illumination of the object to be imaged (living body) with the combined light (frame-sequential light) from the tip of the endoscope 12, it is possible to illuminate, with the narrow-band light (frame-sequential light) required for the inspection with a special light, only the important region in the field of view for inspection to be imaged by the endoscope 12 in a central part of an image. Consequently, the light quantity of the narrow-band light required for the inspection with a special light is reduced, and an excess thermal load is no more imposed on the tip of the endoscope 12 to cause an earlier deterioration thereof.

The present inventor found specific shapes and sizes (dimensions) of the reflective member 44 meeting the conditions as mentioned above, and also found specific focal lengths of two cylindrical lenses constituting the collimator lens 50 for shaping the beam of the narrow-band light in accordance with the shape and size (dimensions) of the reflective member 44. The following description is made in reference to FIGS. 7 and 8.

Figure 7:
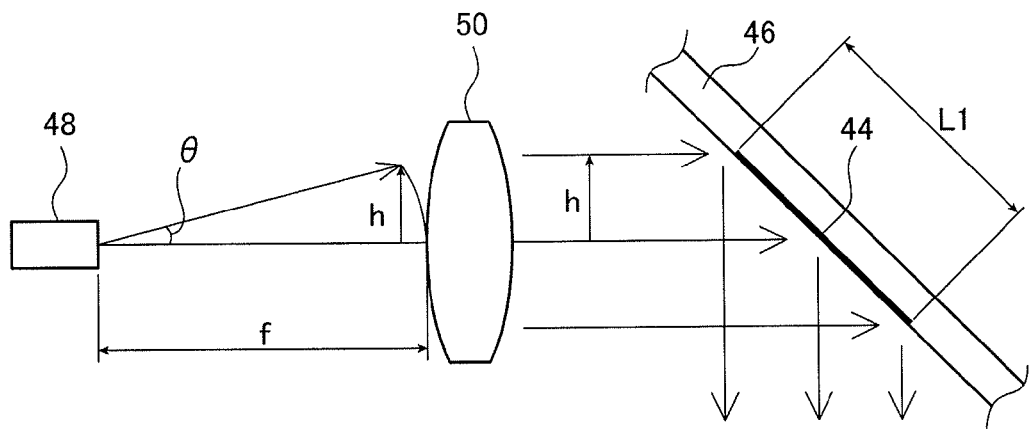
FIG. 7 is a diagram schematically showing an optical path for a narrow-band light extending in the endoscope light source unit of FIG. 2 from a special light source to the light combining member.

In the example as shown in FIG. 7, the special light source 48 as a source of narrow-band light is a semiconductor laser.

It is assumed that a narrow-band light emitted from the semiconductor laser used as the special light source 48 has a divergence angle of about 20° with respect to a direction parallel to an active layer in the semiconductor laser, and a divergence angle of about 10° with respect to a direction perpendicular to an active layer in the semiconductor laser, and that the plane in which the larger divergence angle of the narrow-band light is defined is a plane containing the major axis of the reflective member 44 in an approximately elliptical shape in the light combining member 42, and the optical path of the narrow-band light extending from the special light source 48 to the light combining member 42, namely, the plane of FIG. 7, and the plane in which the smaller divergence angle of the narrow-band light is defined is a plane containing the minor axis of the reflective member 44 and the optical path of the narrow-band light, namely, a plane perpendicular to the plane of FIG. 7.

Figure 8:
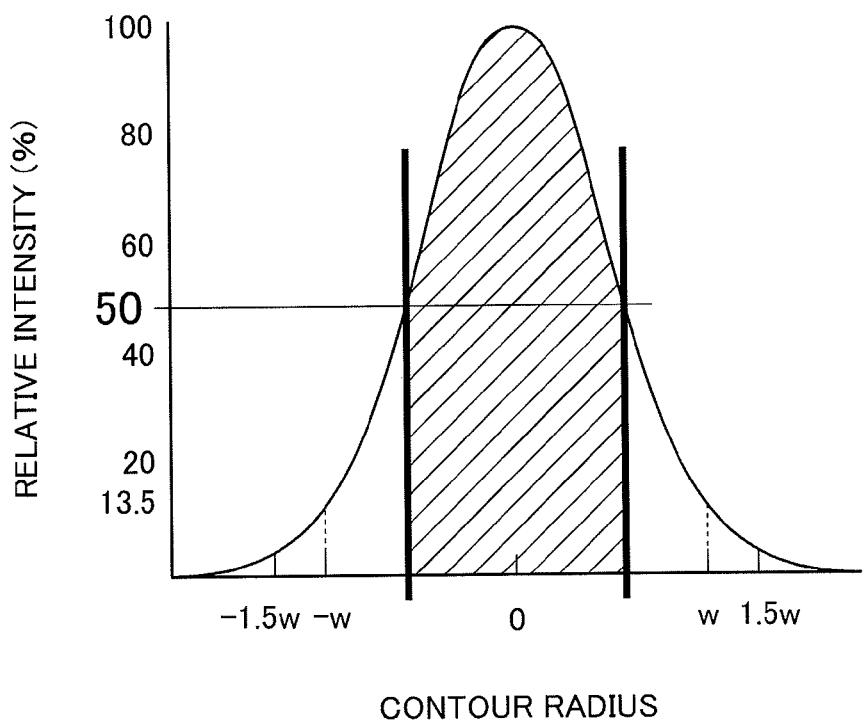
FIG. 8 is a graph showing the intensity distribution of a narrow-band light used in an embodiment of the present invention.

The narrow-band light should solely be light included in a hatched area of the graph of FIG. 8 showing the relative intensity of the Gaussian beam, or the narrow-band light as represented by Gaussian distribution, as a function of the contour radius, with the relative intensity being assumed as 100% at the center of contours, that is to say, in an area between two contour radius values at each of which the relative intensity is 50%. Consequently, the narrow-band light to be used is a Gaussian beam with a relative intensity of 50% or higher.

With the 300 W xenon lamp manufactured by PerkinElmer Japan Co., Ltd. as mentioned above being used, a parallel beam of the white light emitted from the xenon light source 38 has a thickness or diameter of 25.4 mm, and the part in the center of the beam where rays of the white light are absent has a diameter of 4.0 mm.

In consequence, the transparent member 46, as being approximately elliptical in shape because the light combining member 42 is placed as tilted at an angle of 45°, has the exit face (transmission face) whose minor axis is 25.4 mm, being equal to the diameter of a parallel beam of the white light, and whose major axis is 35.9 (25.4×√2) mm.

On the other hand, a shape corresponding to the part where rays of the white light are absent is imparted to the reflective member 44, so that the member 44 has a minor axis of 4.0 mm and a major axis of 5.7 (4.0×√2) mm. For this reason, it is adequate that the beam of the narrow-band light as emitted from the special light source 48 is shaped by the collimator lens 50 into a parallel beam with a diameter of 4.0 mm.

In the case where the reflective member 44 has been designed under the conditions as above, the collimator lens 50 will be so designed as to shape the narrow-band light into a circular beam with a diameter of 4.0 mm so that a reflection region defined by a parallel beam of the narrow-band light from the second light source section 30 may have a shape identical to that of the reflective member 44, namely, an elliptical shape with a minor axis of 4.0 mm and a major axis of 5.7 mm.

Description is now made on a relationship formed between the emission point of the special light source 48 and the focal length of the collimator lens 50 under the use of the light combining member 42 as described above.

It is assumed that, in FIG. 7, the beam of the narrow-band light as emitted from the special light source 48 is shaped by the collimator lens 50 into a circular beam so that the beam of the narrow-band light incident on the reflective member 44 in the light combining member 42 may have shape and size on the reflective member 44 identical to the shape and size of the reflection face of the member 44.

Assuming that the collimator lens 50 has a power in a direction parallel to the plane of FIG. 7, and forms an image in this direction, equation (1) below is formulated as the formula for image formation irrespective of the plane in which the divergence angle is defined:

$$h = f \cdot \sin \theta \quad (1)$$

where θ is the divergence half-angle of a narrow-band light, such as the laser beam from the special light source 48, f is the focal length of the collimator lens 50, and h is the image height of the beam of the narrow-band light as shaped by the collimator lens 50.

In FIG. 7, the length (major axis of an approximately elliptical shape) of the reflective member 44 in the light combining member 42 is indicated with L1. Assuming that the width (minor axis of an approximately elliptical shape) of the reflective member 44 as found in a direction perpendicular to the plane of FIG. 7 is represented by L2, although not shown, equations (2) and (3) below are formulated. It should be noted that L2 can also be considered to represent the diameter of a parallel beam of the narrow-band light as shaped by the collimator lens 50.

$$h = (L1/2) \cdot \sin 45° \quad (2)$$

$$h = L2/2 \quad (3)$$

In the plane of FIG. 7, θ is 10° because a narrow-band light from the light source 48 has a larger divergence angle of about 20° as described above. With L1 being 5.7 mm, the focal length in a direction parallel to the plane of FIG. 7, focal length $f_w$, is therefore derived as follows.

$$f_w \cdot \sin 10° = (5.7/2) \times \sin 45°$$

$$f_w \approx 12 \text{ (mm)}$$

Thus, the collimator lens 50 for shaping the beam of a narrow-band light into a circular beam with a diameter of 4.0 mm should include a cylindrical lens with a focal length of about 12 mm having a power only in a direction parallel to the plane of FIG. 7, in order to modify the beam diameter in the plane of FIG. 7, namely, the plane in which the larger divergence angle of the narrow-band light is defined.

On the other hand, in a plane perpendicular to the plane of FIG. 7, θ is 5° because a narrow-band light from the light source 48 has a smaller divergence angle of about 10°. With L2 being 4.0 mm, the focal length in a direction perpendicular to the plane of FIG. 7, focal length $f_n$ is therefore derived as follows.

$$f_n \cdot \sin 5° = 4/2$$

$$f_n \approx 23 \text{ (mm)}$$

Thus, the collimator lens 50 for shaping the beam of a narrow-band light into a circular beam with a diameter of 4.0 mm should include a cylindrical lens with a focal length of about 23 mm having a power only in a direction perpendicular to the plane of FIG. 7, in order to modify the beam diameter in a plane perpendicular to the plane of FIG. 7, that is to say, in the plane in which the smaller divergence angle of the narrow-band light is defined.

By using the collimator lens 50 which consists of two cylindrical lenses having their respective focal lengths in different directions, it is possible to shape the beam of a narrow-band light into a beam in an approximately circular shape corresponding to the shape and dimensions of the reflective member 44 in the light combining member 42 as described above, and cause an approximately circular beam of the narrow-band light as shaped to be incident on the reflective member 44. As a result, the narrow-band light is combined with white light so that the beam of the former may be located in a central part of the beam of the latter, and, accordingly, the reduction of the white light in light quantity in a specified wavelength range is restricted. During both the inspection with a special light and the normal inspection, the image which is of high accuracy, and bright as a whole can be obtained, allowing a sophisticated endoscopic diagnosis.

In the endoscopy system 10 as shown in FIG. 1, white light and a narrow-band light (frame-sequential lights) in a combined light emitted from the endoscope light source unit 14 of the present invention enter into the optic fiber 32 of the endoscope 12 through the exit end face 56c of the rod integrator 56 of the endoscope light source unit 14 at their respective numerical apertures (NAs), and are propagated through the optical fiber 32 while maintaining the numerical apertures upon entrance, then emitted through the illumination port 24A of the endoscope 12.

To be more specific: In the present invention, a narrow-band light is combined with white light by the light combining member 42 so that the beam of the former may be located in the central part of the beam of the latter where the light quantity is reduced, and the beam of a combined light (frame-sequential light) consisting of the beam of the narrow-band light located in the center and the beam of the white light surrounding the beam of the narrow-band light is converged by the condenser lens 52, with relative locations of the beams of the narrow-band light and the white light being kept as such, so as to cause the whole beam of the combined light to enter into the rod integrator 56, whereupon the white light is incident as light with a larger NA, while the narrow-band light is incident as light with a smaller NA. The white light and the narrow-band light in the combined light are then propagated through the rod integrator 56 without changing their respective NAs, when the in-plane light quantity distribution is equalized. Subsequently, the white light and the narrow-band light are emitted to cause them to enter into the optical fiber 32 of the endoscope 12. The two types of lights are also propagated through the optical fiber 32 without changing their respective NAs, and the object to be imaged (living body) is illuminated with the combined light emitted from the tip of the optical fiber 32, that is to say, through the illumination port 24A of the endoscope 12, the combined light which is prepared by combining together the narrow-band light with a smaller NA arranged in a central part and the white light with a larger NA arranged in a marginal part.

In consequence, the object to be imaged (living body) is illuminated chiefly with the narrow-band light in a central part of the region to be illuminated with the combined light, and chiefly with the white light in a marginal part of the region.

Figure 9:
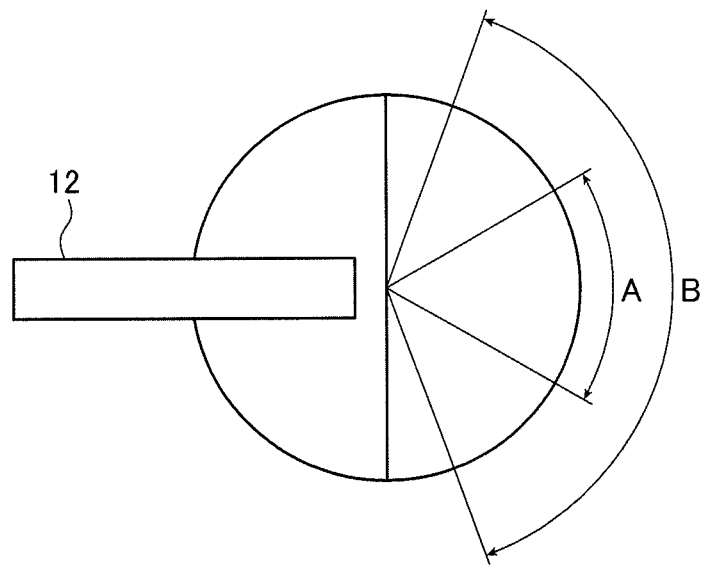
FIG. 9 is a diagram schematically showing the angle of view of an endoscope in the endoscopy system as shown in FIG. 1, and the range of illumination with a special light.

In FIG. 9, the range of illumination with the narrow-band light in the combined light emitted from the endoscope light source unit of the present invention is indicated with A, and assumed to be an angle of 60°. The range of illumination with the white light as indicated with B is assumed to be an angle of 140° corresponding to the angle of view of a common endoscope. If the illuminance is uniform, the energy required for illumination is proportional to the area of a partial spherical surface according to the angle of view. In the case of range A of illumination as an angle of 60°, the energy for illumination is merely about one fifth (0.842/4.134) as compared with the case of range B as an angle of 140°, as seen from equations (4) and (5) below. Used in the equations is the definition of radian: 1 rad≈57.3°.

Thus in the present invention, the illumination with a narrow-band light during the inspection with a special light is concentrated on a specified region of the field of view for inspection so as to secure an adequate light quantity. The reduction of white light in light quantity in a specified wavelength range is avoided during the normal inspection, while, during the inspection with a special light, the output light quantity does not need to be excessively increased with respect to the narrow-band light in order to make a brighter image displayed, that is to say, an unwanted thermal load is not imposed on an endoscopy instrument, especially a tip portion thereof, or even on the living body as a target for inspection, so that the living body is not affected, not damaged for instance, and the tip portion is not deteriorated either by an unwanted thermal load. In consequence, the image to be observed is not rendered darker as a whole either in the inspection with a special light or the normal inspection, giving an image of high accuracy enabling a sophisticated diagnosis.

Area of a partial spherical surface defined by an angle 140° as the angle of view B (range B of illumination with the white light):

$$\int_0^{2\pi}\left(\int_0^{\frac{70}{57.3}}\sin(\theta)d\theta\right)d\phi = 4.134 \quad (4)$$

Area of a partial spherical surface defined by an angle 60° as range A of illumination with the narrow-band light:

$$\int_0^{2\pi}\left(\int_0^{\frac{30}{57.3}}\sin(\theta)d\theta\right)d\phi = 0.842 \quad (5)$$

Figure 10:
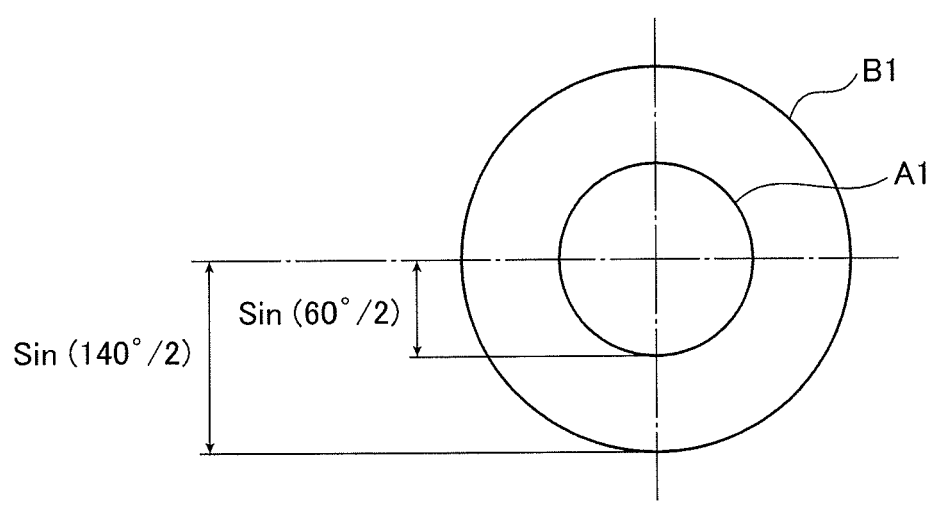
FIG. 10 is a diagram schematically showing the ranges of illumination with white light and a special light in an image made on the endoscopy system of the present invention.

An endoscopic image is generally distorted in its margin, and has a characteristic calculated as f·sin θ. An image obtained with an angle of view B of 140°, and range A of illumination as an angle of 60° which is expected in the image are schematically depicted in FIG. 10 as regions B1 and A1, respectively. Since sin (60°/2) is 0.5, and sin (140°/2) is about 0.94, the diameter ratio between regions A1 and B1 is about 1:2 and, accordingly, the area ratio is about 1:4.

It is well known that an endoscopic image may be distorted to inaccuracy in its marginal part, so that what is considered by an inspector as important is a central part of the image. If an image is of high accuracy in region A1, it is indifferent whether or not the image is dark and blur in a part other than region A1.

Thus in the present invention, the illumination with a narrow-band light during the inspection with a special light is concentrated on a specified region of the field of view for inspection so as to secure an adequate light quantity. The reduction of white light for illumination in light quantity in a specified wavelength range is avoided during the normal inspection, while, during the inspection with a special light, disadvantages due to thermal load are well prevented. In consequence, either in the inspection with a special light or the normal inspection, the accuracy of an image does not decrease in the field of view for inspection in which illumination is carried out with the white light or the narrow-band light, and the image to be observed is not rendered darker as a whole, which makes it possible to obtain, in the field of view for inspection, an image of high accuracy enabling a sophisticated diagnosis.

While the description as above is made on the case where the light combining member 42 is placed as tilted at an angle of 45° (so that the reflection face of the reflective member 44 may form an angle of 45° with the direction in which the white light travels), the light combining member 42 may also be positioned at the intersection of the white light and the narrow-band light in such a manner that it is tilted at an angle of 30° to 60° to the direction in which the white light travels. In that case, assuming that the light combining member 42 is tilted at an angle of θ (the angle between the direction in which the white light travels and the reflection face of the reflective member 44 is θ), the narrow-band light should be incident on the reflection face of the reflective member 44 at an angle of incidence of θ so that it may reflect on the reflective member 44 in the direction which is the same as the direction in which the white light travels. Consequently, the special light source (second light source section 30) is mounted so that the narrow-band light may be incident on the light combining member 42 at an angle of incidence of θ.

In this modification also, the shape and size of the reflective member 44 are specified and the collimator lens 50 is designed based on the angle at which the light combining member 24 is tilted, namely an angle of θ, so that the beam of the narrow-band light may be located in the central part of the beam of the white light where the light quantity is reduced.

In the following, description is made on the functions of the endoscopy system 10 having the endoscope light source unite 14.

As described before, the light source unit 14 is provided with the xenon (Xe) light source 38 (of the first light source section 28) used for both the normal light mode and the special light mode, and the special light source 48 (of the second light source section 30) for the special light mode, which may be a violet laser light source (405 LD) or a blue LED, as light emitting elements. The first and second light source sections 28 and 30 are separately controlled by a light source controlling section (not shown) with respect to light emission, so that the light quantity ratio between light emitted from the first light source section 28 (white light) and light emitted from the second light source section 30 (narrow-band light) is variable at will.

In the normal light mode, the white light as emitted from the xenon light source 38 is made by the reflector 40 into a parallel beam, then passes through the light combining member 42. Subsequently, the beam of the white light is sequentially transmitted through the filters of the first filter set of the rotating filter 47 (R1 filter 47r1, G1 filter 47g1, and B1 filter 47b1) so as to produce frame-sequential red, green and blue lights. The frame-sequential lights are sequentially converged by the condenser lens 52 before they sequentially enter into the rod integrator 56.

In the special light mode, the white light as emitted from the xenon light source 38 is made by the reflector 40 into a parallel beam, and the narrow-band light as emitted from the special light source 48 is shaped by the collimator lens 50 into a parallel beam so that the beam may have an approximately circular shape with its diameter being nearly equal to the minor axis of the reflective member 44 in an approximately elliptical shape in the light combining member 42.

The parallel beam of the white light passes through the light combining member 42, while the parallel beam of the narrow-band light so shaped as to have an approximately circular shape is reflected by the reflective member 44, so that the optical path of the narrow-band light and the optical path of the white light are combined together, that is to say, a combined light having the beam of the narrow-band light arranged in its central part and the beam of the white light arranged in its marginal part is prepared by the light combining member 42.

The combined light as prepared by the light combining member 42 is sequentially transmitted through the filters of the second filter set of the rotating filter 47 (G2 filter 47g2, B2 filter 47b2, and light shielding filter 47Cut) so as to produce frame-sequential green and blue lights. The frame-sequential lights sequentially enter into the condenser lens 52, and converged by the condenser lens 52 so that a relative arrangement of the narrow-band light and the white light in the combined light (frame-sequential light) may be maintained. As a consequence, the combined light as prepared from the narrow-band light with a smaller NA arranged in a central part and the white light with a larger NA arranged in a marginal part enters into the rod integrator 56.

In both the normal light mode and the special light mode, the light, namely the white light or the combined light (frame-sequential light), having entered into the rod integrator 56 is repeatedly reflected in the rod integrator 56, so that the light quantity distribution of the light to be emitted is equalized in the exit face. In this regard, the NAs of the narrow-band light and the white light in the combined light are maintained in the rod integrator 56, that is to say, the combined light as emitted from the rod integrator 56 includes the narrow-band light and the white light whose NAs are each kept intact.

Thus in both the normal light mode and the special light mode, the light having passed through the rod integrator 56 has an equalized light quantity distribution, and is as such inputted into the optical fiber (light guide) 32 to transport it to the connector section. The light as transported to the connector section is then propagated to the tip of the endoscope 12 through the optical fiber 32 constituting an optical system for illumination. In the case of the special light mode, the combined light is propagated through the optical fiber 32 with the NAs of the narrow-band light and the white light being maintained.

As described before, not only the frame-sequential lights obtained from the white light in the normal light mode but those obtained from the combined light prepared from the white light and the narrow-band light in the special light mode are emitted through the illumination port 24A at the tip of the endoscope 12 toward the region to be inspected of a subject. The combined light in the special light mode is emitted for illumination while having the NAs of the narrow-band light and the white light maintained.

The lights coming back from the region to be inspected as illuminated with the frame-sequential lights sequentially form images on the light receiving face of the image pickup device 26 through the light receiving section 24B, that is to say, the region to be inspected is imaged by the image pickup device 26 so as to obtain images thereof having the colors of the frame-sequential lights, respectively.

After imaging, image signals representing the obtained images in their respective colors are outputted from the image pickup device 26, and inputted into the image processing system 36 of the processor 16 through the scope cable 34.

The image signals representing the images in their respective colors as obtained by the image pickup device 26 are subjected to the image processing by a signal processing system including the image processing system 36 of the processor 16, and outputted to the monitor 20 or a recorder (not shown) as the color image to be observed by a user.

In the special light mode, region A1 imaged under the illumination with the narrow-band light in the combined light may be bordered on the obtained image in order to make the region readily visible.

The embodiment as described above is adapted to carry out frame-sequential imaging by using the rotating filter 47 to produce frame-sequence lights from the white light and the combined light, illuminating a target for imaging with the frame-sequential lights, and causing the lights coming back from the target for imaging to form images on the image pickup device (image sensor) 26 of a monochromatic type, although the present invention is not limited to this configuration. A configuration for carrying out simultaneous imaging by using a color image pickup device instead of the rotating filter 47 is also available.

No limitations are imposed on the present invention by the above-detailed embodiment of the endoscope light source unit of the present invention and the endoscopy system including the inventive light source unit. Various improvements or modifications can be made without departing from the gist of the present invention.

What is claimed is:

1. An endoscope light source unit, comprising:
   a first light source section emitting a first illumination light composed of white light;
   a second light source section emitting a second illumination light composed of a narrow-band light in a wavelength band narrower than that of the first illumination light, orthogonally to a direction in which the first illumination light travels;
   a light combining member positioned at an intersection of the first and second illumination lights in such a manner that it is tilted at an angle of 30° to 60° to the direction in which the first illumination light travels, which member has a reflection section located in its center for reflecting at least the second illumination light, and a transmission section surrounding the reflection section for transmitting the first illumination light, the light combining member transmitting the first illumination light through the transmission section and, at the same time, reflecting the second illumination light by means of the reflection section to form a combined light of the first and second illumination lights so that a beam of the second illumination light may be located in a central part of a beam of the first illumination light, wherein the reflection section of the light combining member is approximately elliptical in shape and has a length of at least one of a major or minor axis which is 10 to 50% against a length of at least one of a major or minor axis of an approximately elliptical shape formed on the light combining member by the first illumination light transmitted through the transmission section;
   a shaping lens for modifying the beam of the second illumination light emitted from the second light source section so that the beam may be substantially equal to the reflection section of the light combining member in shape and size; and
   a condenser lens for converging the combined light formed by the light combining member so that a beam of the combined light may have a size substantially identical to a size of an entrance face of a light guide in an endoscope, and the beam of the second illumination light in the combined light may be incident on a center of the entrance face of the light guide.

2. The endoscope light source unit according to claim 1, wherein:
   the shaping lens shapes the beam of the second illumination light into an approximately circular beam so that a beam of the narrow-band light incident on the light combining member placed in a tilted manner may be substantially equal in shape and size to the reflection section of the light combining member that is approximately elliptical in shape.

3. The endoscope light source unit according to claim 2, wherein the beam of the second illumination light as shaped by the shaping lens into a beam in the approximately circular shape has a diameter substantially identical to a diameter of a portion with a reduced light quantity distribution present in a center of the beam of the first illumination light.

4. The endoscope light source unit according to claim 1, wherein the light combining member is placed in such a manner that it is tilted at an angle of 45° to the direction in which the first illumination light travels and a direction in which the second illumination light travels.

5. The endoscope light source unit according to claim 1, further comprising a rod integrator positioned between the condenser lens and the entrance face of the light guide, wherein:
   the rod integrator comprises
   an entrance face on which the combined light as converged by the condenser lens is incident,
   a main body for multiply reflecting therein the combined light entering through the entrance face of the rod integrator into the body to equalize light quantity distribution, and
   an exit face through which the combined light with an equalized light quantity distribution is emitted to the entrance face of the light guide;
   the rod integrator being substantially equal to the light guide in size; and
   the condenser lens converging the combined light so that it may have a size substantially identical to a size of the entrance face of the rod integrator, and the beam of the second illumination light in the combined light may be incident on a center of the entrance face of the rod integrator.

6. The endoscope light source unit according to claim 1, wherein the reflection section of the light combining member has an area of 1 to 25% against an area of a total exit face of the light combining member for emitting the combined light.

7. The endoscope light source unit according to claim 1, wherein the first light source section comprises a discharge tube as a light source.

8. The endoscope light source unit according to claim 7, wherein the discharge tube is a xenon lamp.

9. The endoscope light source unit according to claim 1, wherein the second light source section comprises a semiconductor light source.

10. The endoscope light source unit according to claim 9, wherein the semiconductor light source is one of a blue laser light source, a violet laser light source, and a blue LED.

11. The endoscope light source unit according to claim 1, wherein the reflection section of the light combining member comprises a reflective mirror.

12. The endoscope light source unit according to claim 1, wherein the reflection section of the light combining member comprises a dichroic mirror.

13. An endoscopy system, comprising:
the endoscope light source unit according to claim 1; and
an endoscope having a light guide and positioned so that an entrance face of the light guide may be opposite to the condenser lens of the endoscope light source unit.

14. The endoscopy system according to claim 13, wherein the combined light is emitted from a tip of the endoscope toward an object to be imaged, and a range of illumination with the second illumination light in the combined light has a diameter about half of that of a range of illumination with the first illumination light in the combined light.

* * * * *